(12) United States Patent
Kamler

(10) Patent No.: US 9,504,472 B2
(45) Date of Patent: Nov. 29, 2016

(54) LIGATOR AND METHOD OF USE

(71) Applicant: Alpine Medical Devices, LLC, Reno, NV (US)

(72) Inventor: Jan P. Kamler, Reno, NV (US)

(73) Assignee: Alpine Medical Devices, LLC, Reno, NV (US)

( * ) Notice: Subject to any disclaimer, the term of this patent is extended or adjusted under 35 U.S.C. 154(b) by 0 days.

(21) Appl. No.: 14/642,503

(22) Filed: Mar. 9, 2015

(65) Prior Publication Data
US 2015/0173766 A1 Jun. 25, 2015

Related U.S. Application Data

(63) Continuation of application No. 13/834,087, filed on Mar. 15, 2013, now Pat. No. 8,974,474.

(60) Provisional application No. 61/701,357, filed on Sep. 14, 2012, provisional application No. 61/707,111, filed on Sep. 28, 2012.

(51) Int. Cl.
*A61B 17/12* (2006.01)
*A61B 17/128* (2006.01)

(52) U.S. Cl.
CPC ....... *A61B 17/12013* (2013.01); *A61B 17/128* (2013.01); *A61B 17/1285* (2013.01); *A61B 2017/12018* (2013.01); *F04C 2270/0421* (2013.01)

(58) Field of Classification Search
CPC .............. A61B 17/12013; A61B 2017/12018; A61B 1/00066; A61B 1/00121; A61B 1/00128; A61B 1/0052
See application file for complete search history.

(56) References Cited

U.S. PATENT DOCUMENTS 3,760,810 A 9/1973 Van Hoorn
3,967,625 A 7/1976 Yoon
(Continued)

FOREIGN PATENT DOCUMENTS

CN 86203090 U 4/1987
CN 2036031 U 4/1989
(Continued)

OTHER PUBLICATIONS

Wikipedia; Endoscopy; 7 pgs.; retrieved from the internet Sep. 28, 2012 (http://en.wikipedia.org/wiki/Endoscopy).

*Primary Examiner* — Julian W Woo
*Assistant Examiner* — Shaun L David
(74) *Attorney, Agent, or Firm* — Shay Glenn LLP

(57) ABSTRACT

A ligating system having a ligating apparatus configured to attach to a distal end of a scope and to hold a ligating band thereon; an activating cord configured to extend down a working channel of the scope and attach to the ligating apparatus; and a line pulling assembly including: a central body; an attachment mechanism on the central body configured to attach the line pulling assembly to a proximal end of the scope; an access channel through the central body and in communication with the working channel of the scope, the access channel providing an open inlet to the working channel of the scope when the line pulling assembly is attached to the proximal end of the scope; and a winding mechanism attached to the central body, wherein the winding mechanism is configured to pull the activating cord proximally such that the ligating band is removed from the ligating apparatus.

21 Claims, 15 Drawing Sheets

(56) References Cited

U.S. PATENT DOCUMENTS

| | | | |
|---|---|---|---|
| 4,226,239 A | 10/1980 | Polk et al. | |
| 4,735,194 A | 4/1988 | Stiegmann | |
| 5,203,863 A | 4/1993 | Bidoia | |
| 5,320,630 A * | 6/1994 | Ahmed | 606/140 |
| 5,356,416 A | 10/1994 | Chu et al. | |
| 5,462,559 A * | 10/1995 | Ahmed | 606/140 |
| 5,507,797 A | 4/1996 | Suzuki et al. | |
| 5,569,268 A | 10/1996 | Hosoda | |
| 5,624,453 A | 4/1997 | Ahmed | |
| 5,643,293 A | 7/1997 | Kogasaka et al. | |
| 5,735,861 A * | 4/1998 | Peifer et al. | 606/139 |
| 5,741,273 A | 4/1998 | O'Regan | |
| 5,788,715 A | 8/1998 | Watson et al. | |
| 6,007,551 A * | 12/1999 | Peifer et al. | 606/140 |
| 6,059,719 A * | 5/2000 | Yamamoto et al. | 600/127 |
| 6,136,009 A | 10/2000 | Mears | |
| 6,235,040 B1 | 5/2001 | Chu et al. | |
| 6,547,798 B1 | 4/2003 | Yoon et al. | |
| 6,610,072 B1 | 8/2003 | Christy et al. | |
| 6,685,713 B1 * | 2/2004 | Ahmed | 606/140 |
| 6,730,101 B1 * | 5/2004 | Peifer et al. | 606/140 |
| 6,923,756 B2 | 8/2005 | Sudakov et al. | |
| 7,037,314 B2 | 5/2006 | Armstrong | |
| 7,189,247 B1 * | 3/2007 | Zirps et al. | 606/140 |
| 8,062,308 B2 | 11/2011 | Noda et al. | |
| 8,974,474 B2 | 3/2015 | Kamler | |
| 2002/0026199 A1 | 2/2002 | Fortier et al. | |
| 2002/0072757 A1 | 6/2002 | Ahmed et al. | |
| 2004/0006256 A1 * | 1/2004 | Suzuki et al. | 600/140 |
| 2005/0277955 A1 | 12/2005 | Palmer et al. | |
| 2006/0058816 A1 | 3/2006 | Hassanien | |
| 2006/0089660 A1 * | 4/2006 | Saeed et al. | 606/139 |
| 2006/0122632 A1 | 6/2006 | Hassanien et al. | |
| 2006/0161170 A1 | 7/2006 | DeLuca et al. | |
| 2006/0259041 A1 | 11/2006 | Hoffman et al. | |
| 2007/0093855 A1 * | 4/2007 | Zhang | 606/140 |
| 2007/0118162 A1 | 5/2007 | Abi-Kheirs | |
| 2008/0004622 A1 | 1/2008 | Coe et al. | |
| 2008/0009668 A1 | 1/2008 | Cohn | |
| 2008/0255412 A1 | 10/2008 | Surti | |
| 2008/0287965 A1 | 11/2008 | Ducharme | |
| 2009/0131748 A1 * | 5/2009 | Chami | 600/106 |
| 2009/0198255 A1 | 8/2009 | Ikeda | |
| 2010/0063517 A1 | 3/2010 | Cleator | |
| 2011/0077666 A1 | 3/2011 | McCahon et al. | |
| 2012/0078272 A1 | 3/2012 | Smith | |
| 2013/0226198 A1 | 8/2013 | Kamler | |

FOREIGN PATENT DOCUMENTS

| | | |
|---|---|---|
| CN | 201067419 Y | 6/2008 |
| CN | 201067420 Y | 6/2008 |
| EP | 1147744 A2 | 10/2001 |
| GB | 1334560 A | 10/1973 |
| GB | 2426459 A | 11/2006 |
| JP | 04312745 B2 | 8/2009 |
| WO | WO 96/24292 A1 | 8/1996 |
| WO | WO99/65400 A1 | 12/1999 |
| WO | WO2004/021865 A2 | 3/2004 |
| WO | WO2007/079674 A1 | 7/2007 |
| WO | WO2009/144694 A1 | 12/2009 |

* cited by examiner

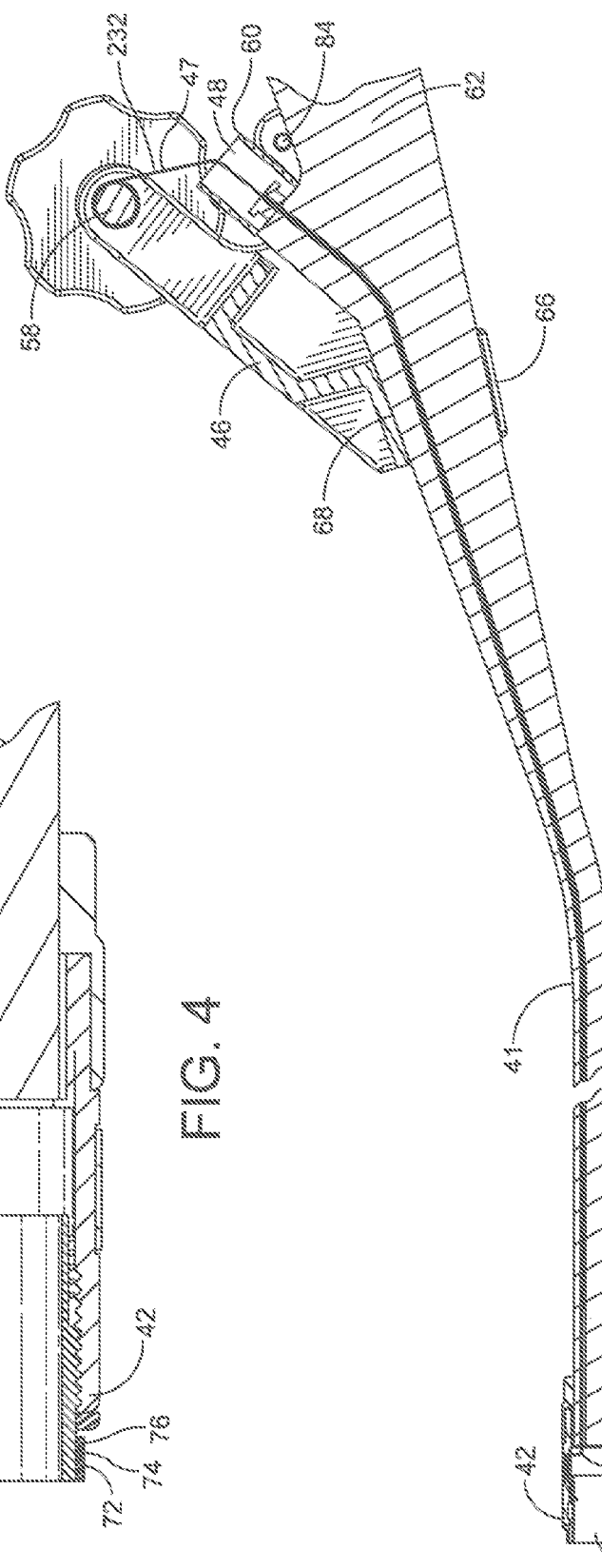

LIGATOR AND METHOD OF USE

CROSS REFERENCE TO RELATED APPLICATIONS

This application is a continuation of U.S. application Ser. No. 13/834,087, filed Mar. 15, 2013, which application claims the benefit of priority of U.S. Provisional Applications No. 61/701,357, filed Sep. 14, 2012, and No. 61/707,111, filed Sep. 28, 2012, all of which are hereby incorporated by reference in their entirety.

FIELD

The present disclosure is directed to a ligator apparatus and method, and in one particular embodiment, to an esophageal ligator and method of esophageal ligation.

BACKGROUND

Methods for treatment of varices and general ligation methods have long been known in the art. This has long been so for both for human and non-human tissues.

Esophageal varices are enlarged esophageal veins. These frequently complicate chronic liver disease. Esophageal varices may rupture and bleed, potentially leading to death. Ligation of the varices can be performed to treat acutely bleeding varices. Ligation can also be performed preventatively to destroy the varices before they start to bleed. During the process of ligation, varices are suctioned into a hollow space of the ligator and bands are released over the tissue to strangulate it. Strangulation leads to death of the tissue and subsequent scarring obliterates the varices.

The process of ligation can be further effectuated with an endoscope or other device for accessing or penetrating internal aspects of a human, an animal, a fish, or other entity. Endoscopes generally consist of a rigid or flexible tube, a light delivery system, a lens system to transmit images from the object being viewed to the viewer, and an additional channel coupled to the rigid or flexible tube to allow entry of medical instruments.

Currently used variceal ligators manufactured by Wilson Cook and Boston Scientific, use string with attached beads to pull the rubber band off the cylinder that is attached to the tip of the endoscope. A string is pulled via the working channel of the endoscope and via an inner opened part of the cylinder. The string is then split into two parts (two strings) to which beads are attached. These two strings are then placed over the opposite side of the cylinder. Rubber bands are then placed over the strings in a way that each band is separated by a single bead on both sides of the cylinder. When the string is pulled, beads pull rubber bands separately over the edge of the front part of the cylinder and ligate the tissue suctioned in the cylinder. Pulling of the string is performed by a mechanical device attached to the hand of the scope. The mechanical device consists of a knob to which the string is attached. When the knob is rotated by an operator, the string wraps around its central part thus pulling the string and by shortening it, releases the band from the attached cylinder to the tip of the endoscope. As a result, the rubber bands and beads of these variceal ligators cause the outer surface of the cylinder that is to be inserted into the body to be course, thus making it more difficult to insert the ligator into smaller orifices. Furthermore, these devices are not designed for reloading bands.

Other prior art devices include a single band device. These devices allow release of a single band only off the surface of the inner cylinder being pulled inside the outer cylinder by a simple pull of the string. These devices do not provide releasing of multiple bands.

Another prior art ligator is disclosed in U.S. Pat. No. 7,641,652 to Koe et al. channel (the "Koe reference"). The Koe reference discloses a large ligating device mounted substantially spaced from the end of an endoscope. The Koe device includes a mounting arm and other structure surrounding the penetrating end of the endoscope, and the ligating device is transverse to the endoscope viewing component. The Koe device blocks the operator's view of the material to be ligated, so it renders the ligating process difficult and requires significant operator training to use the device with relative accuracy. The Koe device also is bulky and includes substantial edges, wire (including rotating wire), and other components that make introduction into the esophagus difficult, if not impossible.

SUMMARY OF THE DISCLOSURE

The applicant has recognized shortcomings of the prior art devices. As a result, the applicant has developed a generally tubular ligator mountable to an endoscope with the axis of the ligator generally aligned with an axis of the working end of the endoscope. In some embodiments, the axis of the ligator in parallel to, and in some embodiments coaxial with, the central axis of the working end of the endoscope. The ligator pushes one or more ligation bands off the end of the ligator by rotating around the ligator axis, and thereby moving, a first ligator structure with respect to a second ligator structure.

In certain embodiments, the rotation is caused by pulling a line or other component. In some embodiments, this component extends from the ligator through a working channel of the endoscope. In some instances, a portion the line wraps around or along the surface or periphery of the first or second ligator structure and is pulled at a substantial angle to, and in some embodiments transversely to, the axis of the ligator.

In certain embodiments, the first ligator structure is a first cylinder, and the second ligator structure is a second cylinder having a differing diameter than the first cylinder. In some embodiments, cylinders have mating threaded sections and associated structure, such as for example, the pulling line causing the relative rotation of the first and second cylinder.

In some embodiments, the relative rotation of the cylinders causes one cylinder portion to urge a ligator band off of a second cylinder portion. In some instances, the ligator includes a mount for mounting the ligator to the working end of an endoscope.

Methods of operation of the ligator are also disclosed herein. In one embodiment, an operator causes the relative rotation of the cylinders to urge a ligation band onto adjacent structure, such as bulging or other tissue for example. In some embodiments, this relative rotation is caused by pulling of a line or other link between the ligator and operator. In some embodiments, the relative rotation forces a ligation band to move off of one of the ligator cylinders.

In some embodiments, the operator can see through the ligator during use of the ligator on the working end of the endoscope.

Some embodiments include a novel line or cord pulling assembly. This assembly can include an indexed line puller to controllably pull the line in predetermined increments. Certain embodiments can include opposed arcuate mounting arms; and if desired the opposed arcuate mounting arms can provide a mounting channel, allowing structure, such as endoscope, to pass through the channel. Some cord pulling assemblies can include a securing member, such as a transverse removable pin for example, to help secure the cord pulling assembly in position on, for example, an endoscope. In some instances, the arcuate mounting arms and securing member cooperatively secure the endoscope in position. The latter arrangement can make the cord pulling assembly easy to mount on a device (such as an endoscope for example), secure in position for use, and later remove from the device on which the assembly was mounted.

There are many other novel features, problem solutions, advantages, and aspects of the present disclosure. They will become apparent as the specification proceeds.

There are other aspects and advantages of the present apparatus and methods disclosed by the present specification. They will become apparent as the specification proceeds. In this regard, it is to be understood that the Background and this Brief Summary are not intended to be limiting, and thus the scope of the invention is to be determined by the claims as issued and not whether given subject matter addresses an issue noted in the Background or includes subject matter recited in this Brief Summary.

BRIEF DESCRIPTION OF THE DRAWINGS

The applicants' preferred and other embodiments are further disclosed in association with the accompanying drawings, in which:

FIG. 3 is a cross-sectional view taken along section line 3-3 of FIG. 2;

FIG. 4 is an expanded partial cross-sectional view of the ligating end of the ligator apparatus shown in the cross-sectional view of FIG. 3;

It is to be understood that specially-orienting terms, such as top, bottom, front, back, upwardly, or downwardly are used to explain relative orientation of structures as shown in the Figures and as the structures might be used. They are not to be construed, however, to require such an orientation in space.

DETAILED DESCRIPTION

FIGS. 1-29 depict ligators and other structures that can be utilized to ligate flesh such as one or more esophageal varices. These ligators, others including various of their features, and varying associated ligator components and methods can be variously used to ligate other material, human or otherwise.

Figure 1:
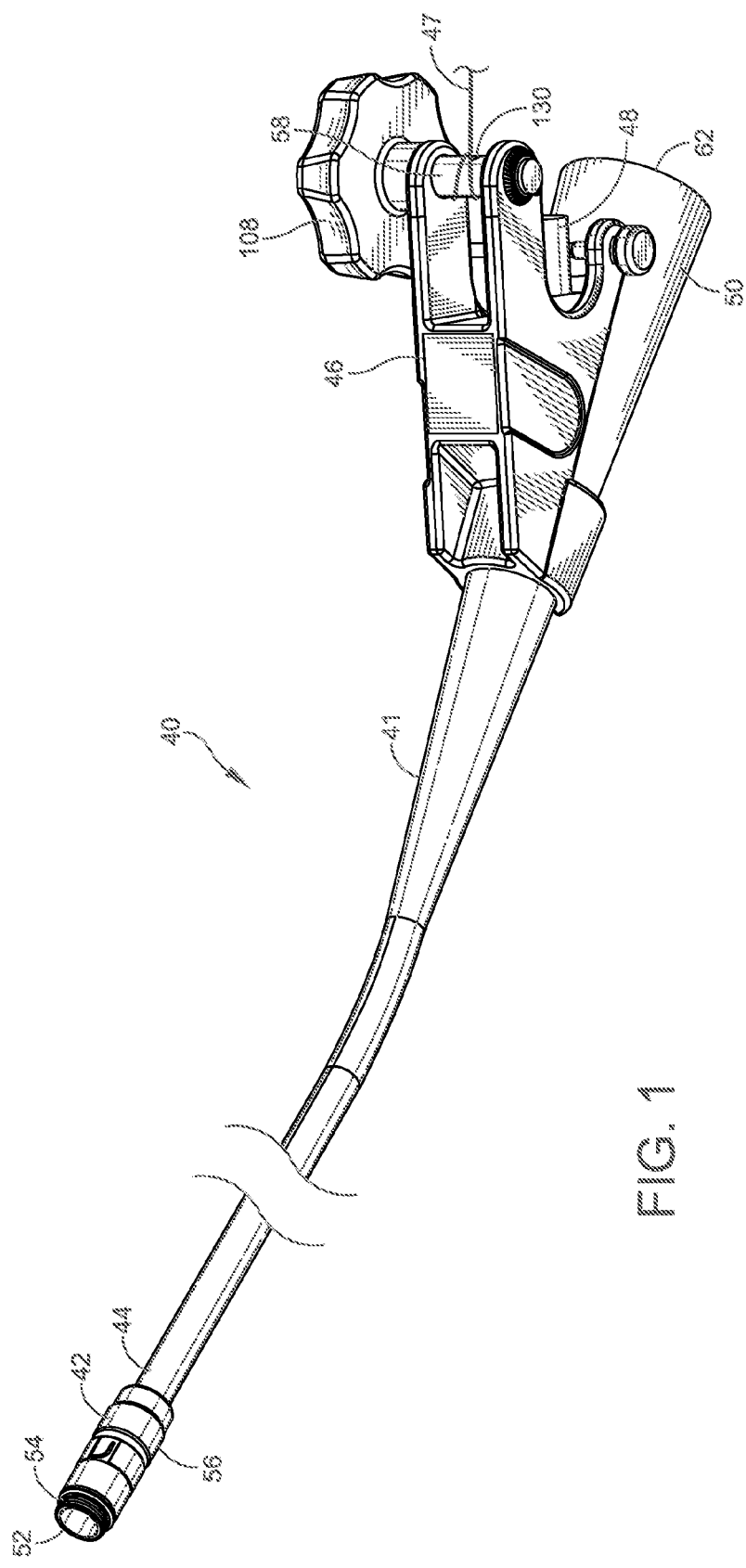
FIG. 1 is a perspective view of one embodiment of the present ligator apparatus having a ligator mounted on a penetrating end of an endoscope and a cord pulling assembly mounted over.

With reference now to FIG. 1, one embodiment of a ligator assembly, generally 40, includes a generally tubular endoscope 41 with a removable ligator 42 mounted on a penetrating end 44 of the endoscope 41 and a cord pulling assembly 46 removably mounted on an access channel 48 adjacent the control end 50 of the endoscope 41. An operator, such as a medical practitioner for example, can cause the cord pulling assembly 46 to pull a cord 47 through interior of the endoscope 41 and cause the ligating end 52 of the ligator 42 to eject a ligating band 54. The particular endoscope 41 shown in FIG. 1 is an Olympus Video Gastroscope.

Figure 2:
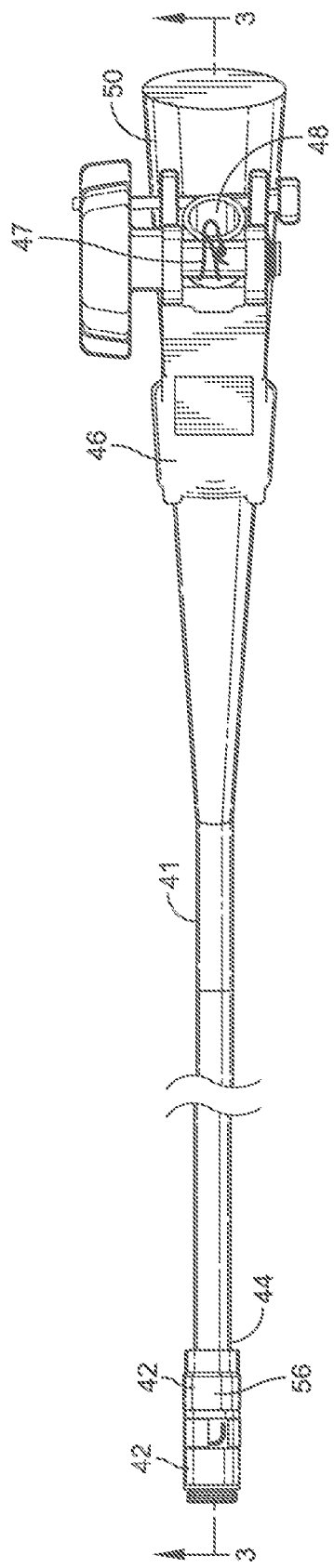
FIG. 2 is a top plan view of the ligator apparatus of FIG. 2.

Turning now to FIG. 2, the ligator 42 is generally tubular and is mounted within a generally tubular elastic mounting adapter 56, which in turn is mounted to the penetrating end 44 of the endoscope 41. On the opposing control end 50 of the endoscope 41, the cord pulling assembly 46 is mounted to surround the access channel 48 in order to pull the cord 47 from the interior of the endoscope 41 through the access channel 48.

Referring now to FIG. 3, the pulling cord 47 extends from pulling rod 58 in the cord pulling assembly 46 through the working channel (not shown) that runs from the outer open end 60 of the access channel 48 through to the open penetrating end 44 of the endoscope 41. For human applications, the pulling cord 47 is FDA-approved material on the ligating end. The pulling cord can be made of one material throughout its length, or it can include an intermediate differing type of cord or connector such as a wire, plastic line, monofilament, braided line, etc.

The interior of the endoscope 41 also includes a user viewing or image transmission channel or member (not shown) that extends from the endoscope viewing lens end 62 to the opposed open penetrating end 44, allowing the operator to see through the endoscope's penetrating end 44 when inserted into a patient's esophagus for example. In turn, the ligator 42 has a central passage 64 that allows light to pass through the center of the endoscope 41, which in turn allows the operator to look through the viewing lens end and see through the penetrating end 44 of the endoscope 41 and the ligator 42 as well.

In this embodiment, the front end 66 of the cord pulling assembly 46 is somewhat conical. This conical front end 66 is adapted to mount about the penetrating end 44 of the endoscope 41 and slide into place abutting a matingly conically configured external periphery 68 of the endoscope 41. Differently configured cord pulling assemblies (not shown) can be shaped differently for differing endoscope configurations.

With reference now to FIG. 4, the pulling cord 47 extends from the penetrating end 41 of the endoscope 41 to enter cord channeling structure, generally 70, in the ligator 42. When the pulling cord 47 is pulled by the cord pulling assembly (46 in FIG. 3), the ligator 42 is driven to eject the end ligating band 54 among the four ligating bands 54, 72, 74, 76 on the end of the ligator 42.

Figure 5:
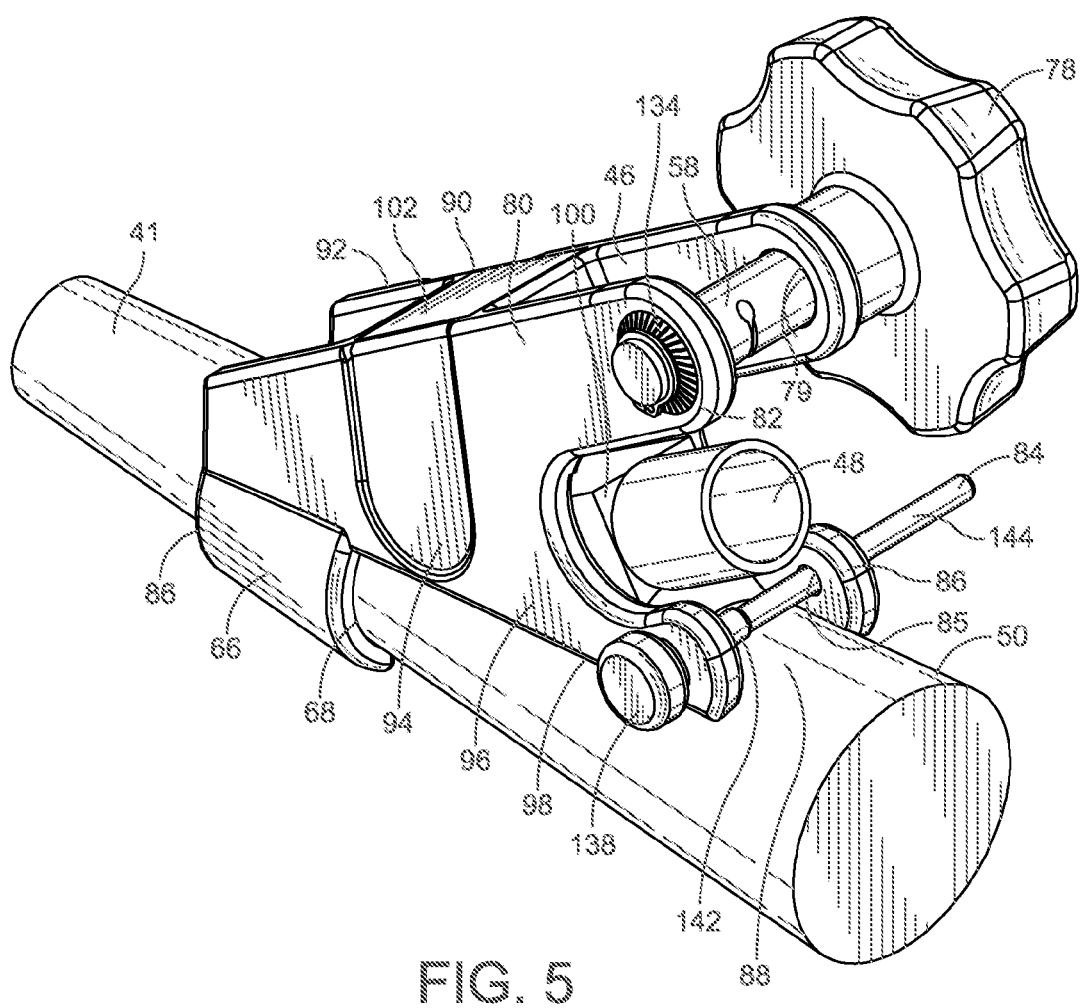
FIG. 5 is an expanded partial perspective view of the cord pulling apparatus mounted adjacent the endoscope control end as shown in FIG. 1.

With reference to FIG. 5, the cord pulling assembly 46 includes: (i) an indexed knob 78 at one end of the pulling rod 58 transversely penetrating mating laterally opposed, coaxial knob rod passages, e.g., 79, in the upwardly extending upper end 82 of the central mounting body 80 in the assembly 46; and (ii) a mounting pin 84 transversely penetrating mating laterally opposed, coaxial mounting pin passages, e.g., 85, a lower end 86 of the central mounting body 80 adjacent the outer periphery 88 of the control end 50 of the endoscope 41. The components of the cord pulling assembly can be made from a variety of materials, such as for example plastic, various metals, rubber, etc.

Figure 6:
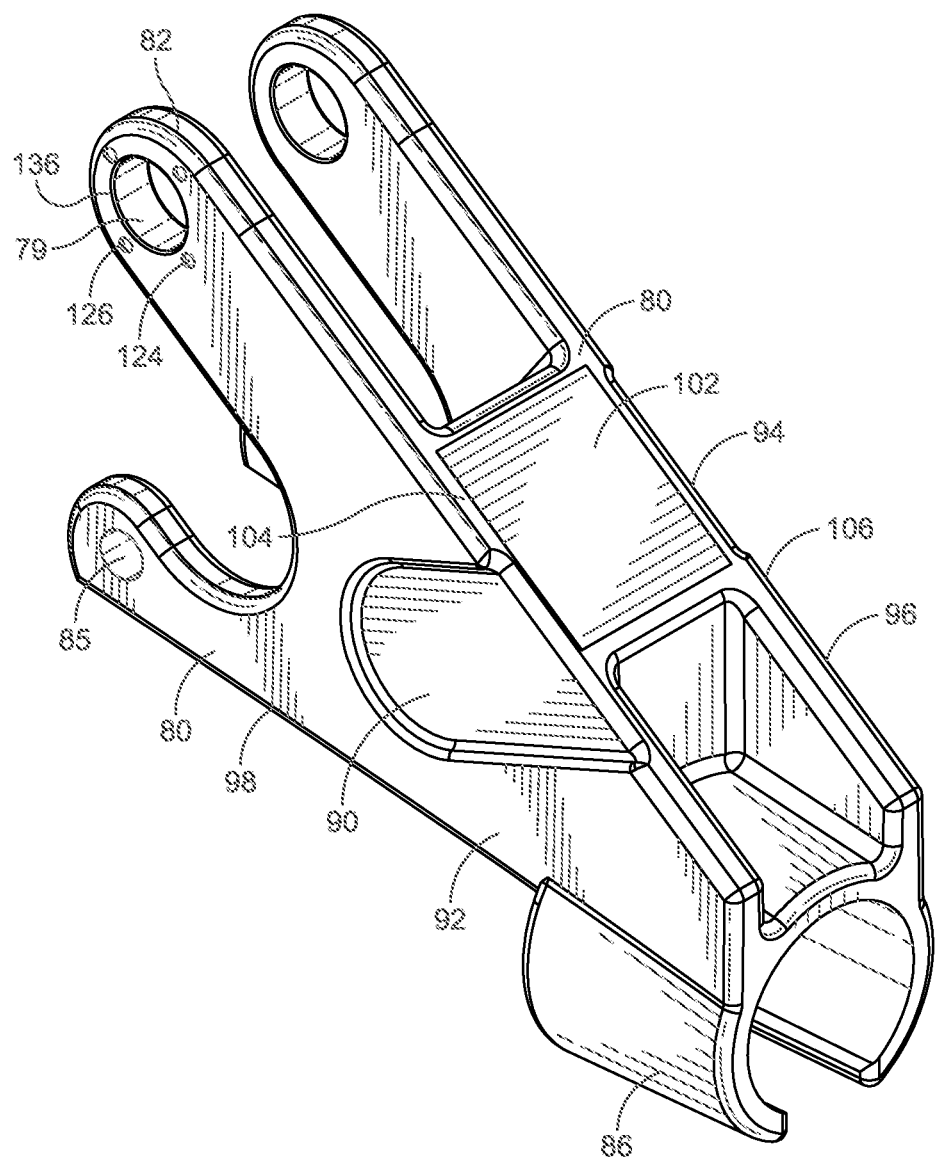
FIG. 6 is a perspective view of the cord pulling frame of the cord pulling assembly of FIG. 5.

Referring to FIGS. 5 and 6, the central mounting body 80 of the cord pulling assembly 46 (see FIG. 5) has: (i) an upwardly extending and outwardly facing thumb-grip depression or channel 90 on one laterally extending, generally planar side 92 intermediate the upwardly extending end 82 and the lower end 86 of the mounting body 80; and (ii) an upwardly extending and outwardly facing finger-grip depression or channel 94 on the opposed laterally extending, generally planar side 96 of the mounting body 80, also intermediate the upwardly extending end 82 and the lower end 86 on the mounting body 80. With reference to both FIGS. 5 and 6, the thumb-grip depression 90 extends at an acute angle to one laterally extending bottom edge 98 of the mounting body 80, and the finger-grip depression 94 is nearly transverse to the opposed bottom edge 99. The one bottom edge 98 and opposed bottom edge 99 are coplanar and at a slightly acute angle to, and spaced upwardly from, the axis of the generally conical front end 66 of the mounting body 80. A top side planar frame member 102 extends between the opposed upwardly extending top lateral edges 104, 106 intermediate and interconnecting the opposed thumb grip depression 90 and finger grip depression 94.

Referring back to FIG. 5, the central mounting body 80 includes an endoscope access channel passage 100 intermediate the pulling rod 58 and the mounting pin 84. This passage 100 allows an endoscope access channel 48 to open relatively directly below and adjacent the pulling rod 58 and above and adjacent the mounting pin 84. The axis of the pulling rod 58 is thus laterally transverse to the axis of the access channel 48 and parallel to the axis of the mounting pin 84. Similarly, the axis of the mounting pin 84 and axis of the pulling rod 58 is transverse to the opposed laterally extending sides 92, 96 of the mounting body 80. As shown in FIG. 3, this pin 84 can abut external periphery of the endoscope 41 and secures the cord pulling assembly in position on the endoscope 41 between that abutment and the upwardly extending access channel 48.

Figure 7:
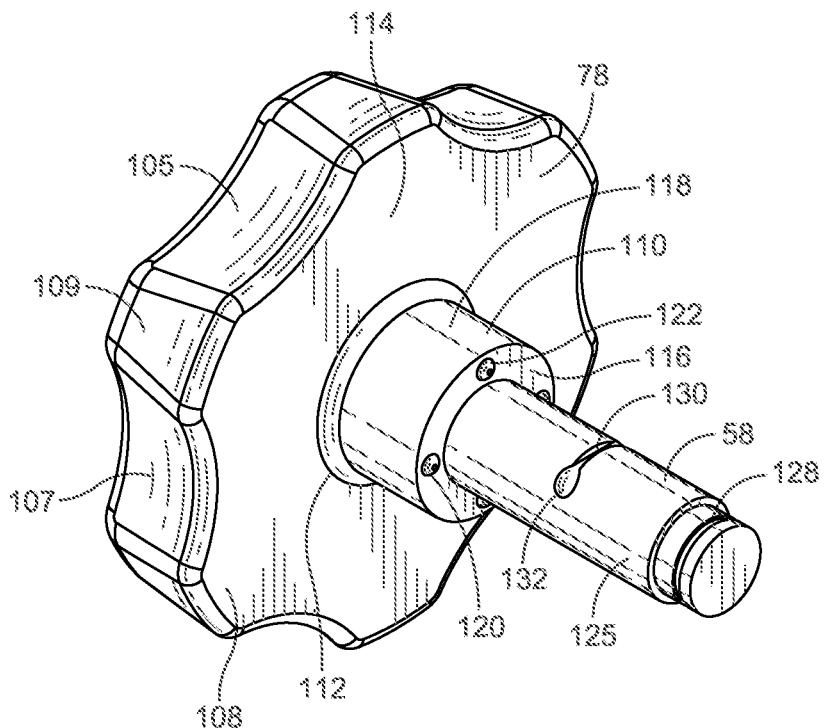
FIG. 7 is a perspective view of indexed pulling knob of the cord pulling apparatus of FIG. 5.

Referring now to FIG. 7, the indexed knob 78 has finger grip depressions or channels, e.g., 105, 107 transverse to the axis of the indexed knob 78 penetrating the otherwise generally circumferential outer periphery 109 of the knob 78. The indexed knob 78 also includes the central pulling rod 58 extending transversely from the axial center (not shown) of a radially outwardly extending knob handle 108.

The handle abutting end (not shown) of rod 58 has a hub section 110 also extending radially outwardly from the central mounting rod 58. The outer edge 112 of the hub section 100 abuts and extends from the generally planar interior side 114 of the knob handle 108. A radially outwardly extending interior hub side 116 extends from the outer periphery of the central rod 58 to the outer radial periphery cylindrical outer surface 118 of the hub section 110.

The interior hub side 116 has four rounded index projections, e.g., 120, 122, extending inwardly in the direction of the rod arm 125 extending from the hub section 110. Each pair of the index projections, e.g., 120, 122, are spaced from each other by an equal distance. The index projections, e.g., 120, 122, penetrate, as shown in FIG. 6, mating index depressions or dimples, e.g., 124, 126, in the mating side 92 of the mounting body 80 surrounding the rod passage 79.

The central rod 58 has a lock washer mounting end 128 opposite the handle abutting end (not shown). A pulling cord slot 130 penetrates the outer periphery of the rod 58 (i) transverse to the axis of the rod 58 and (ii) intermediate the lock washer mounting end 128 and the interior hub side 116. The pulling cord slot 130 has a widened knot mounting channel end 132, providing a cavity for securely seating a pulling cord knot or other similar structure in the pulling cord slot 130.

Referring to FIGS. 5 and 7, a lock washer 134 is mounted on the lock washer mounting end 128 of the central rod 58 to bias the interior hub side 116 against, as shown in FIG. 6, the hub side mating section 136 surrounding the rod passage 79. With reference to FIGS. 5, 6, and 7, the central rod 50 is thereby rotatably mounted within the rod passages, e.g., 79, but is urged to stop (index) as the four mating projections, e.g., 120, 122, penetrate four opposed mating dimples, e.g., 124, 126 due to the biasing provided by the lock washer 134.

Figure 8:
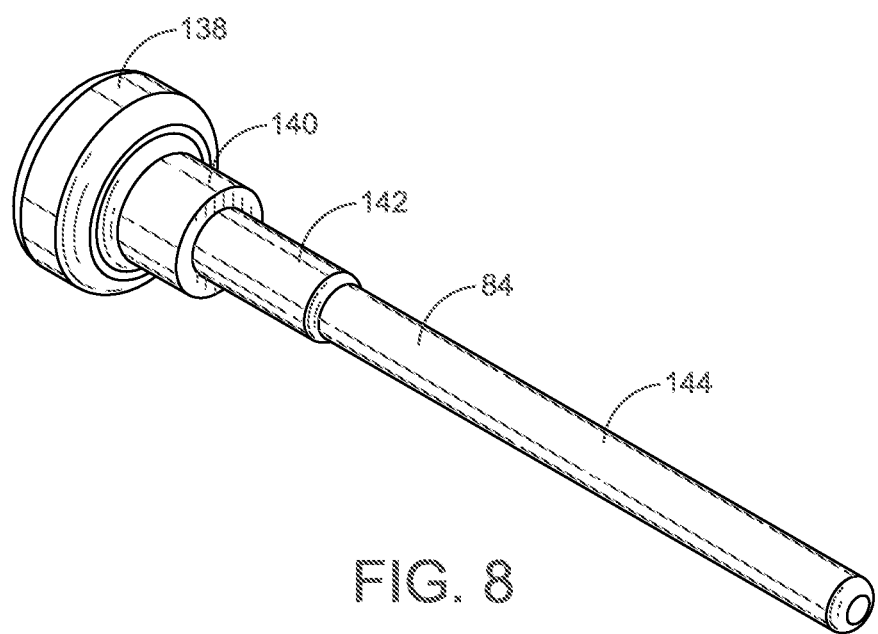
FIG. 8 is a perspective view of the anchor pin of the cord pulling apparatus of FIG. 5.

With reference now to FIG. 8, the mounting pin 84 has a widened mounting knob end 138, a narrower mounting pin hub 140 extending from the mounting knob end 138, a still narrower inner mounting rod section 142 extending from the mounting pin hub 140, and a still narrower end mounting pin rod end 144 extending laterally from the mounting pin section. The knob end 138, pin hub 140, inner mounting rod section 142, and end mounting pin rod 144 are all coaxial with each other.

Figure 9:
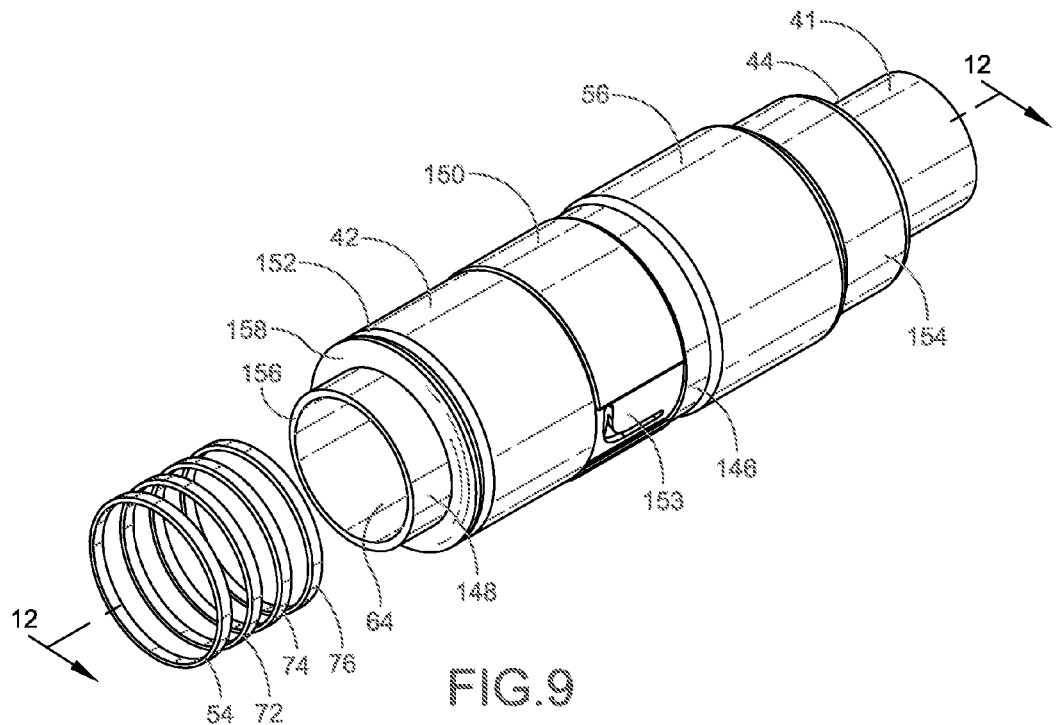
FIG. 9 is a perspective view of the ligator of FIG. 1.

Referring now to FIG. 9, the ligator 42 has a fixed band-ejector outer barrel 146 coaxially surrounding a rotatable band-mounting inner barrel 148. The fixed band-ejector outer barrel 146 is held in a fixed position with respect to the endoscope 41 penetrating end 44 by the mounting end 154 of the outer barrel 146 and by the mounting adapter 56 and its friction grip on the matingly abutting outer periphery (not shown in FIG. 9) of the endoscope penetrating end 44 and ligator 42.

This embodiment of the outer barrel 42 has a band driving end 152 opposite the outer barrel mounting end 154 within the mounting adapter 56. A C-shaped sealing ring 150 (see also FIG. 18) surrounds a central cord slot section 153 in the outer barrel 146 intermediate the band driving end 152 and the mounting end 154 of the ligator 42.

The inner barrel 148 has a band mounting end 156 extending outwardly from the band driving end 152 of the outer barrel 146. A resilient band-driving circular washer 158 (see also FIG. 19) is (i) mounted about, and abuts with a friction grip, the outer periphery of the band mounting end 152 of the inner barrel 148 and (ii) abuts the band driving end 152 of the outer barrel 146.

Figure 10:
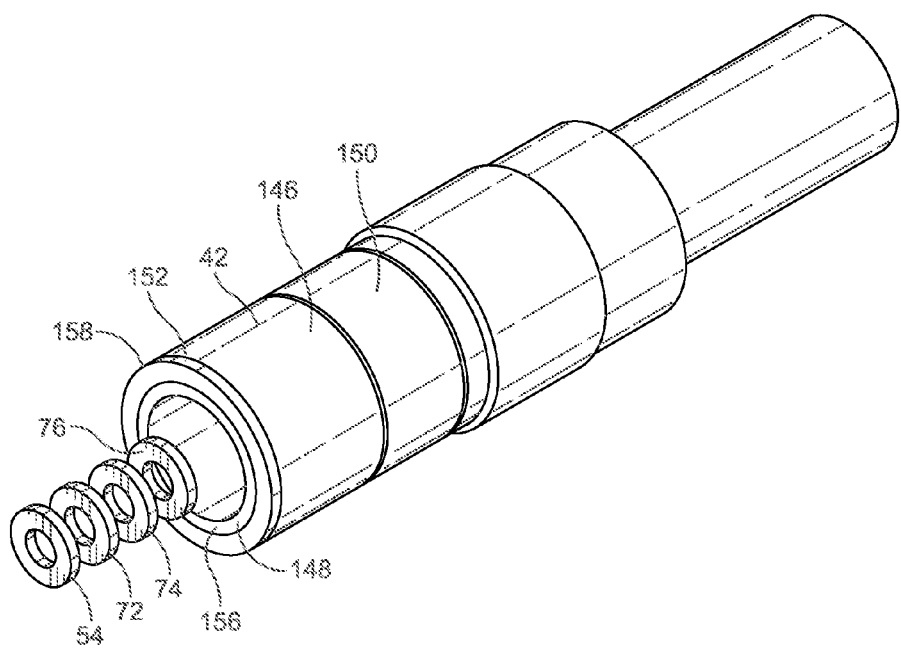
FIG. 10 is a perspective view of the ligator of FIG. 9 but with the outer ring having ejected four bands from the inner ring.

Referring now to FIG. 10, when the inner barrel 148 is rotated by pulling the pulling cord (not shown), the inner barrel 148 moves along the fixed outer barrel 146 and circular washer 158 to drive the ligatures 56, 72, 74, 76 off of the band mounting end 152 of the ligator 42.

Figure 11:
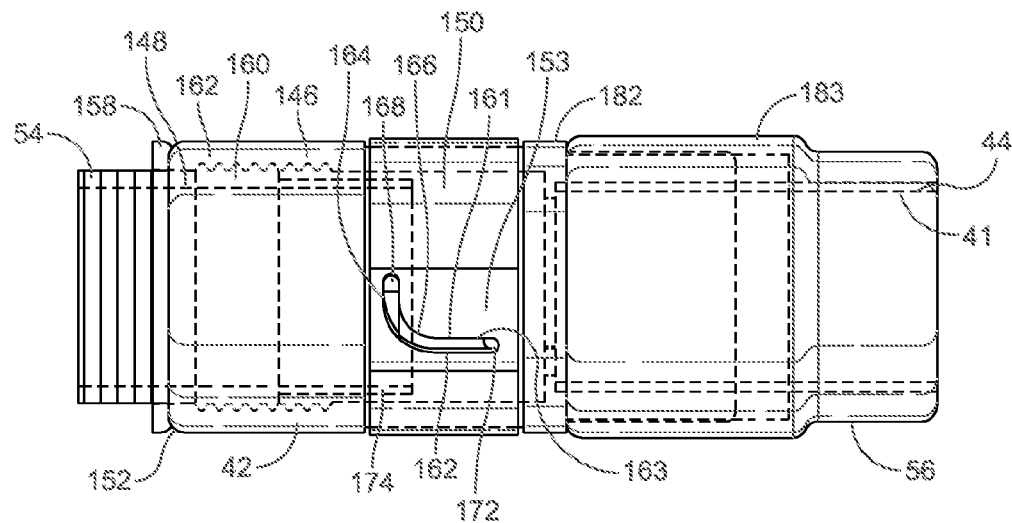
FIG. 11 is a first side elevational view of the ligator of FIG. 9 showing the external cord slot in the outer barrel.

With reference now to FIG. 11, the ligator inner barrel 148 includes a threaded external peripheral section 160 matingly threadable with a threaded internal peripheral section 162 within the outer barrel 146. As a result, rotation of the inner barrel 148 with respect to the outer barrel 146 can drive the inner barrel 148 further into the interior of the outer barrel 146, in turn forcing the band-driving washer 158 to force a ligator band, e.g., 54, of the ligating or band-mounting end 156 of the inner barrel 148.

Figure 14:
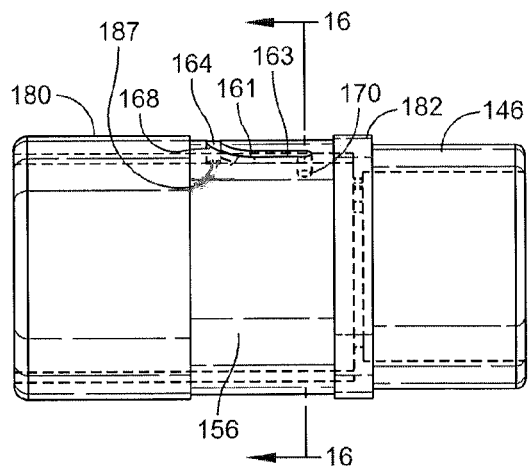
FIG. 14 is a side elevational view of the outer and inner barrels of FIG. 13.
Figure 16:
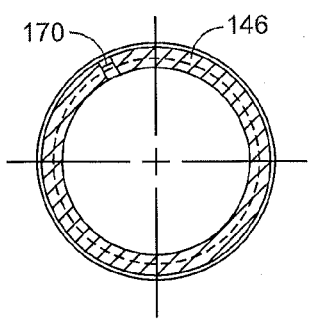
FIG. 16 is a cross-sectional view of the outer barrel taken along section line 16-16 in FIG. 14 (i.e., with the inner barrel not included in this view)

With collective reference now to FIGS. 11, 14, and 16, the outer barrel 146 has a somewhat L-shaped, curved cord channel or depression 161 in the central cord-slot section 153. The cord channel 161 has: (i) a laterally extending section 163 coaxial with both the axis of the ligator 42 and the axis of the penetrating end 44 of the endoscope 41; (ii) a transverse section 164 extending transverse to the laterally extending section 162 and being coplanar with the barrel radius extending from the axis of the outer barrel 146 to the transverse section 164; (iii) a curved cord channel section 166 intermediate and interconnecting the laterally extending section 163 and radially extending section 164; (iv) a first cord passage 168 (see also FIG. 12) at the outer end of the transverse section 164 perpendicularly extending into the interior of the outer barrel from the transverse section 164; and (v) a second cord passage 170 at the outer end of the laterally extending section 163 perpendicularly extending into the interior of the outer barrel 146 from the laterally extending section 163.

Figure 12:
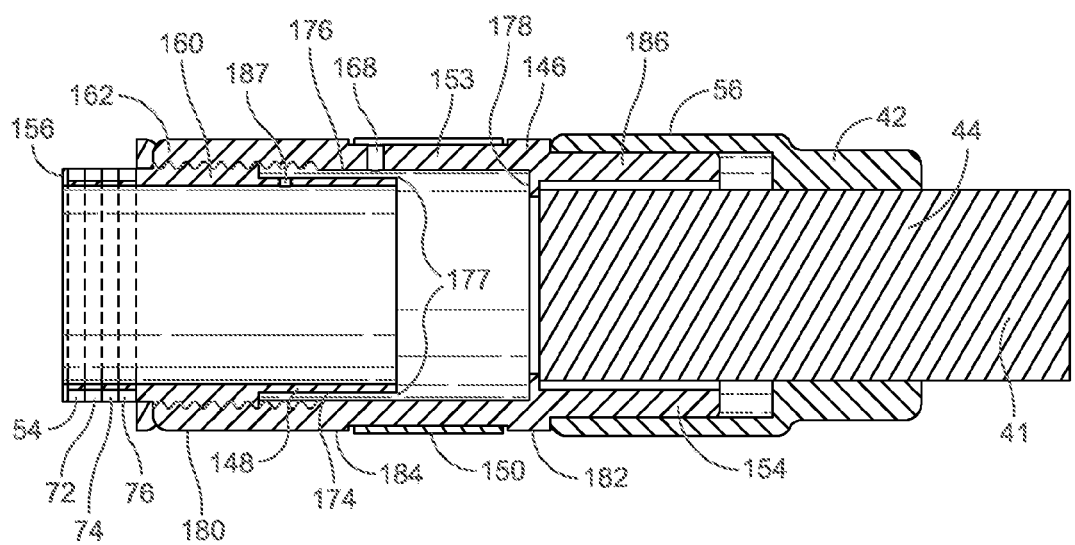
FIG. 12 is a cross-sectional elevational view of the ligator of FIG. 9 taken along section 12-12 of FIG. 9.
Figure 15:
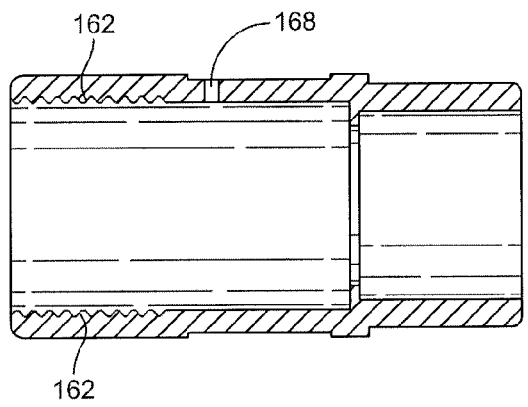
FIG. 15 is a cross-sectional view of the outer barrel taken along section line 15-15 in FIG. 13 (i.e., with the inner barrel not included in this view)

As a result, the pulling cord (not shown in FIG. 11) can pass from the interior of the outer barrel 146 through the second cord passage 170, through the cord channel 161 and back into the interior of the outer barrel 146 through the first cord passage 168. With reference to FIGS. 12 and 15, the first cord passage 168 extends radially inwardly toward the outer periphery of the inner end 174 of the inner barrel 148 and spaced axially laterally from the inner barrel threaded section 162 toward the endoscope penetrating end 44. With reference to FIG. 14, when the inner barrel 148 is rotated and laterally moved within the interior of the outer barrel 146, the first cord passage 168 in the outer barrel 146 is aligned coaxially with an inner barrel cord passage 187 in the inner barrel 148.

Figure 17:
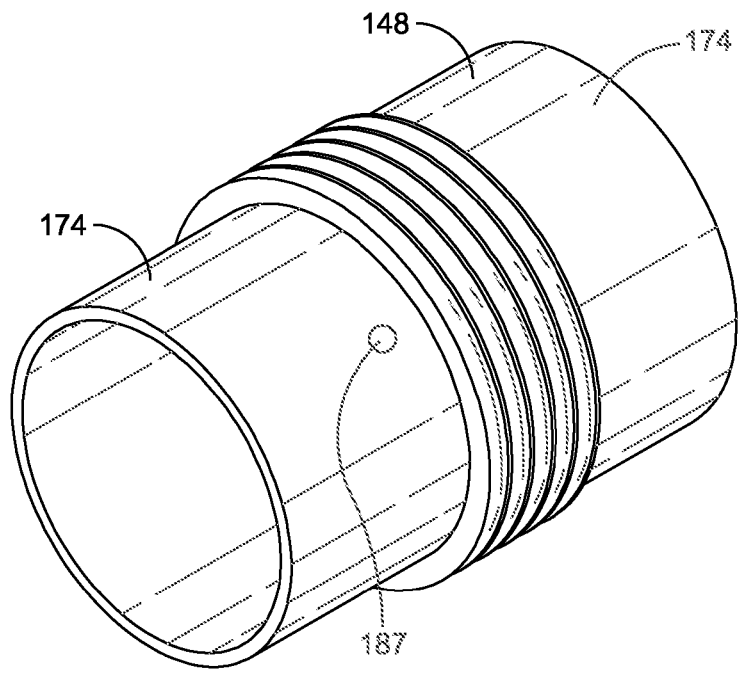
FIG. 17 is a is perspective view of the inner barrel of the ligator of FIG. 9.

With continuing reference to FIG. 12 and additional reference to FIG. 17, the inner end 174 of the inner barrel 148 is tubular. The outer circumference of the inner end 174 is substantially less than the inner circumference of adjacent, surrounding section 176 of the outer barrel 146, providing a cord wrapping area 177 between the inner end 174 and surrounding section 176. A pulling cord (not shown) can thus pass through the first cord passage 168 and wrap around the outer circumference of the inner end 174 within the confines of surrounding section 176 of the outer barrel 146.

With the four ligating bands 54, 72, 74, 76 mounted on the inner barrel 148, the inner end 174 of the inner barrel 148 is spaced laterally from thus penetrating end 44 of the endoscope as well as an interior barrier ridge 178 extending radially inwardly from the interior periphery of the outer barrel 146. This spacing forms penetrable space 180 within the outer barrel 146 into which the inner barrel 148 inner end 174 may move when the inner barrel 148 is rotated in one direction with respect to the outer barrel 146.

Figure 13:
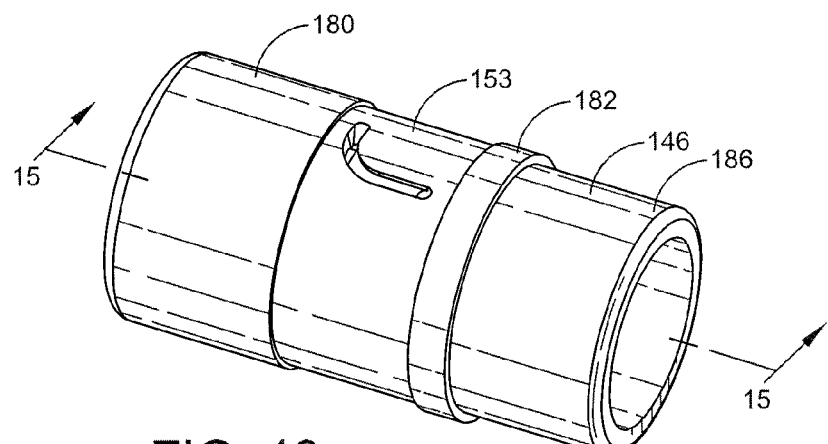
FIG. 13 is a perspective view of the outer barrel of the ligator of FIG. 9 with the inner barrel rotated through multiple threading rotations with respect to the outer barrel and laterally moved completely within the interior of the outer barrel.

Turning now to FIG. 13, the central cord slot section 153 in the outer barrel 146 has a somewhat narrower outer diameter than, and is intermediate and abuts, the band driving section 180 and mid-section 182 in the outer barrel 146. The band driving section 180 and mid-section 182 have the same outer diameter. With reference now to FIG. 11, the outer diameter of widened outer barrel mounting portion 183 of the mounting adapter 56 is (i) wider than the outer diameter of the underlying adapter mounting section 186 of the outer barrel 146, but (ii) only slightly larger than the outer diameter of the mid-section 182, which the mounting adapter 56 abuts.

With reference to FIGS. 12 and 17, the inner barrel 148 has a radially extending cord passage 187 extending radially inwardly from the outer periphery to the inner periphery in the interior end 174 of the inner barrel 148. A pulling cord can thus penetrate this cord passage 187 and be knotted in the interior of the inner barrel 148.

With reference back to FIG. 12, with the sealing ring 150 mounted about and abutting the central cord slot section 153, the external periphery of the collective band driving section 180, sealing ring 150, mid-section 182, and mounting adapter 56 cooperatively provide a relatively smooth outer ligator surface 184 with a relatively narrow cross-section that is (i) readily and easily slidable through the type of human oropharynx into the esophagus with which the given endoscope is designed for use, yet (ii) sufficiently wide for the endoscope operator to see through the interior of the ligator 42.

Figure 18:
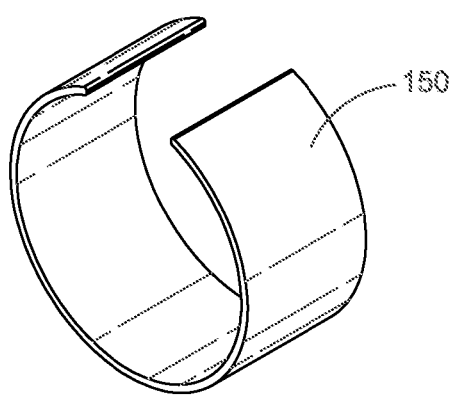
FIG. 18 is a perspective view of the outer sealing ring on the outer barrel of the ligator of FIG. 9.
Figure 19:
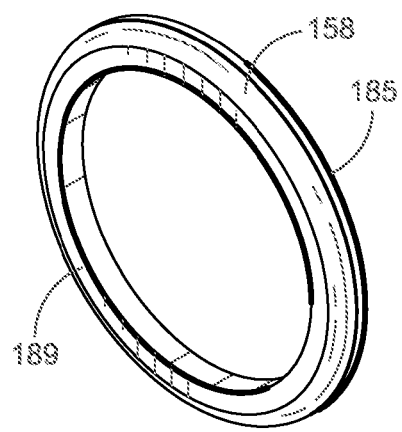
FIG. 19 is a perspective view of the band driving ring abutting the driving end of the outer barrel of the ligator of FIG. 9.

Referring now to FIG. 18, the sealing ring 150 has a somewhat tubular shape. Referring to FIG. 19, the band-driving washer 158 has a thickened band-driving end 185 and a relatively thinner opposed end 189

With reference back to FIG. 11, the outer barrel 146, inner barrel 148 and sealing ring 150 can be made of stainless steel. The band-driving washer 158 can be made out of plastic and the ligating bands, e.g., 54, are commercially available. The mounting adapter 56 can be made of rubber or silicone.

Figure 20:
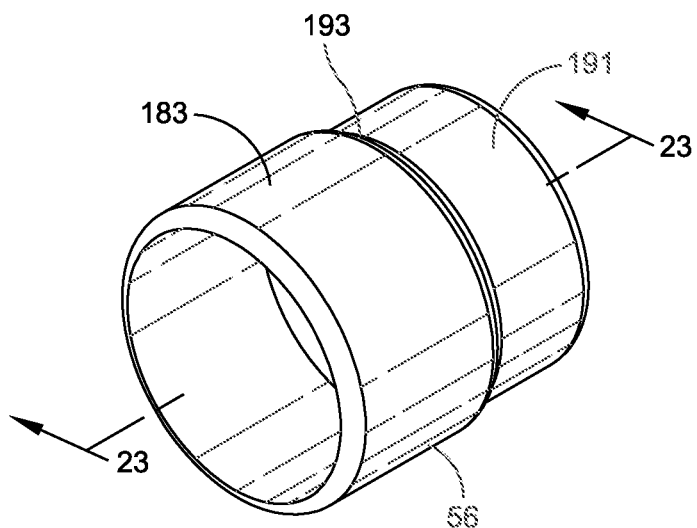
FIG. 20 is a perspective view of the intermediate rubber mounting adapter of FIG. 21.
Figure 21:
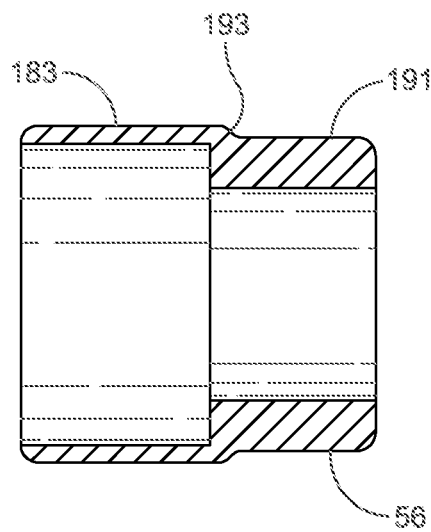
FIG. 21 is a cross-sectional view of the intermediate rubber mounting adapter taken along section line 23-23 of FIG. 22.

With reference now to FIGS. 20 and 21, the mounting adapter 56 has a narrowed endoscope mounting section 191 extending from the widened outer barrel mounting portion 183. A sloped neck 193 joins the outer periphery of the widened outer barrel mounting portion 183 and the outer periphery of the narrowed endoscope mounting section 191.

The mounting adapter 56 is optional. It can be dispensed with particularly when there may be a poor seal between the ligator 42 and the penetrating end 44 of the endoscope 41. When the mounting adapter 56 is not used, the overall diametral width of the ligator 41 is reduced, which can be beneficial to reduce the level of contact of the ligator 41 with surrounding flesh for example.

Figure 22:
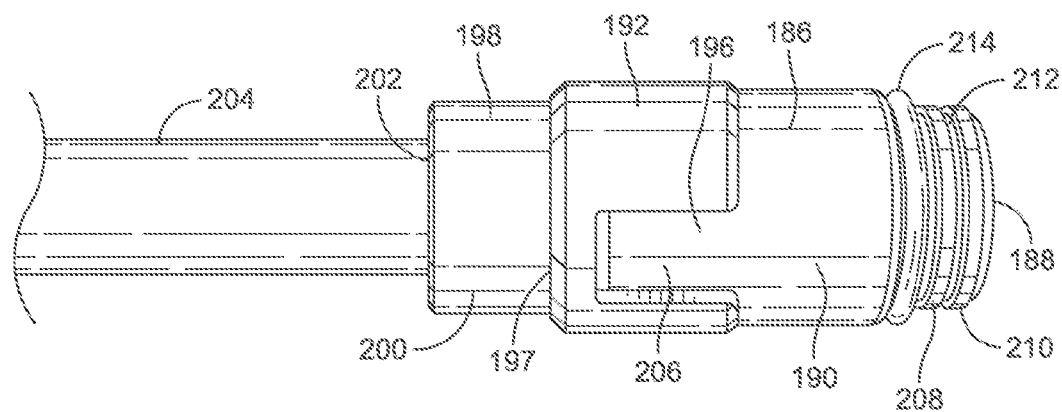
FIG. 22 is a side plan view of an alternative ligator mounted directly to the penetrating end of an endoscope.

Referring now to FIG. 22, an alternative embodiment of a ligator 186 includes an inner band-bearing barrel 188 mounted within an outer band-driving barrel 190 and a cord slot seal tube 192 rotatably mounted about (and friction gripping) the mid-section 196 of the outer barrel 190. A narrowed outer barrel mounting section 198 extends from the mid-section 196 through a central ring passage 197 in the seal tube 192 and provides a friction grip mount 200 about the penetrating end 202 of an endoscope 204.

The seal tube 192 includes a laterally extending cord slot access channel 206. The cord slot access channel 206 provides operator access to an outer barrel access channel (not shown) and mating passages (not shown) into the interior of the outer barrel 190 in the fashion described above when the seal tube 192 is rotated to expose a cord access channel (not shown) within the cord slot access channel 206 in the seal tube 196 (such cord access channel being structured as described above for the access channel 160). Stretched ligating bands 208, 210 are friction-fit mounted about the band-bearing section 212 of the inner barrel 188 adjacent a band-driving rubber ring or band driving washer 214 friction-grip mounted on the band-bearing section 212 to abut the opposed band-driving end 214 of the outer barrel 190.

Figure 23:
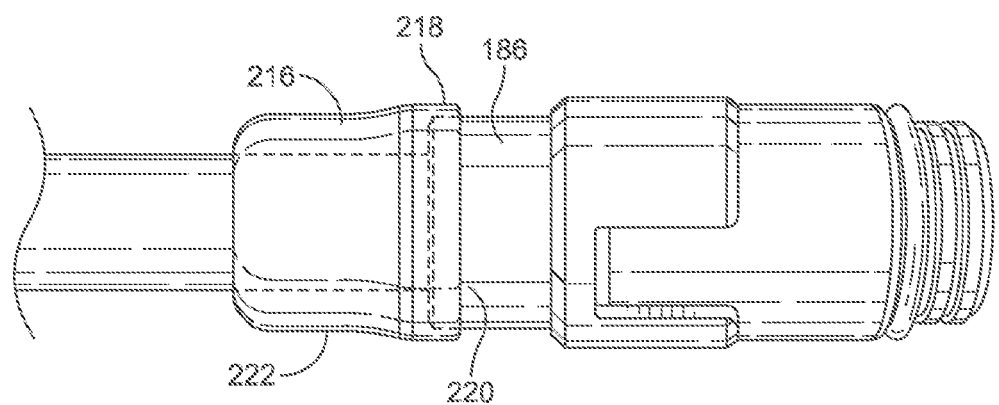
FIG. 23 is side plan view of an embodiment of the ligator of FIG. 20 mounted via an intermediate rubber mounting adapter to the penetrating end of an endoscope.

With reference now to FIG. 23, an alternative method of mounting the ligator 186 utilizes a somewhat tubular rubber mounting adapter 216 friction fit on one end 218 about the external periphery of the mounting end 220 of the ligator 186 and friction fit on the opposed, narrower end 222 about the external periphery of the penetrating end 202 of the endoscope 204.

Figure 24:
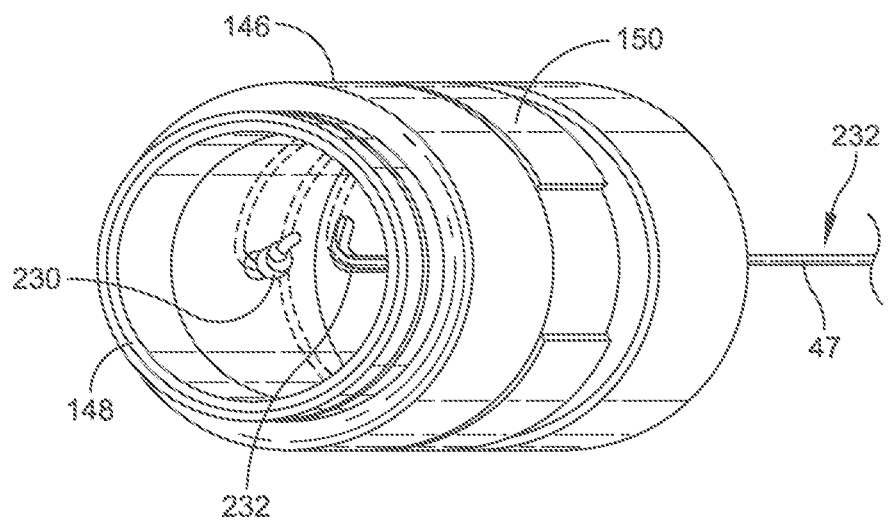
FIG. 24 is a perspective view of a pulling cord installed in the outer barrel of the ligator of FIG. 1.
Figure 25:
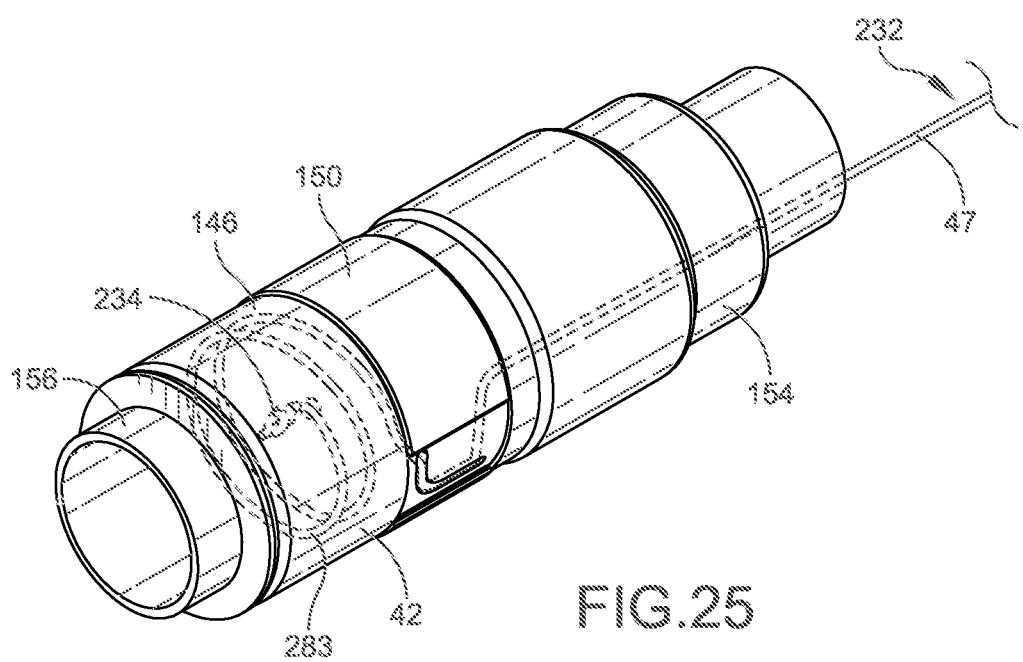
FIG. 25 is a somewhat perspective view of the cord-bearing ligator outer barrel of FIG. 24 mounted onto the cord-bearing inner barrel of FIG. 25.
Figure 26:
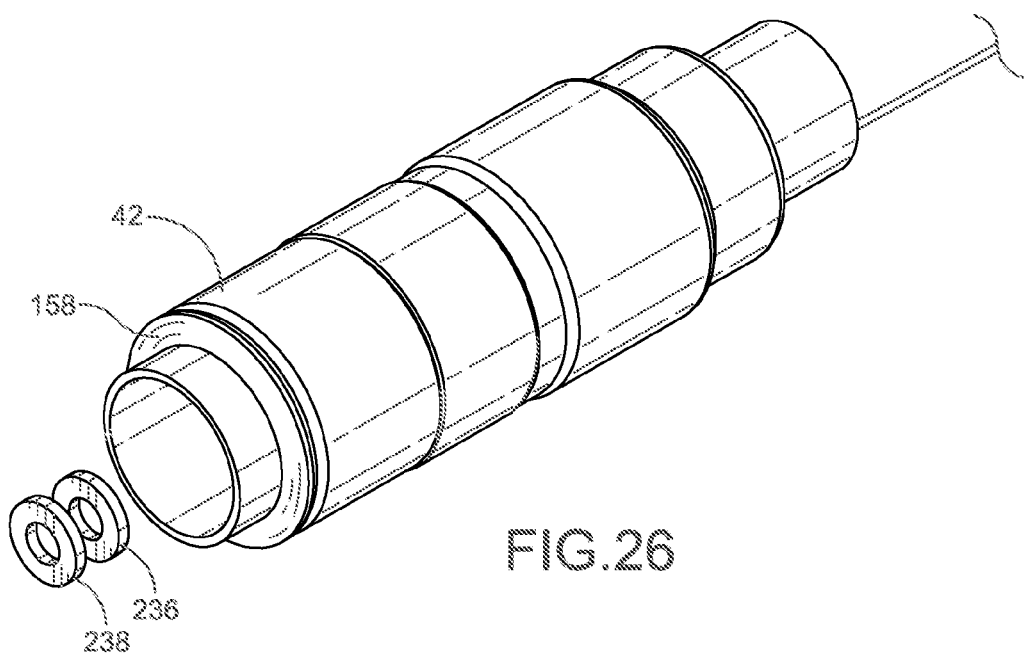
FIG. 26 is a somewhat perspective view of the outer and inner barrels of FIG. 26 with ligating bands (ligatures) aligned for mounting on the ligator inner barrel.
Figure 27:
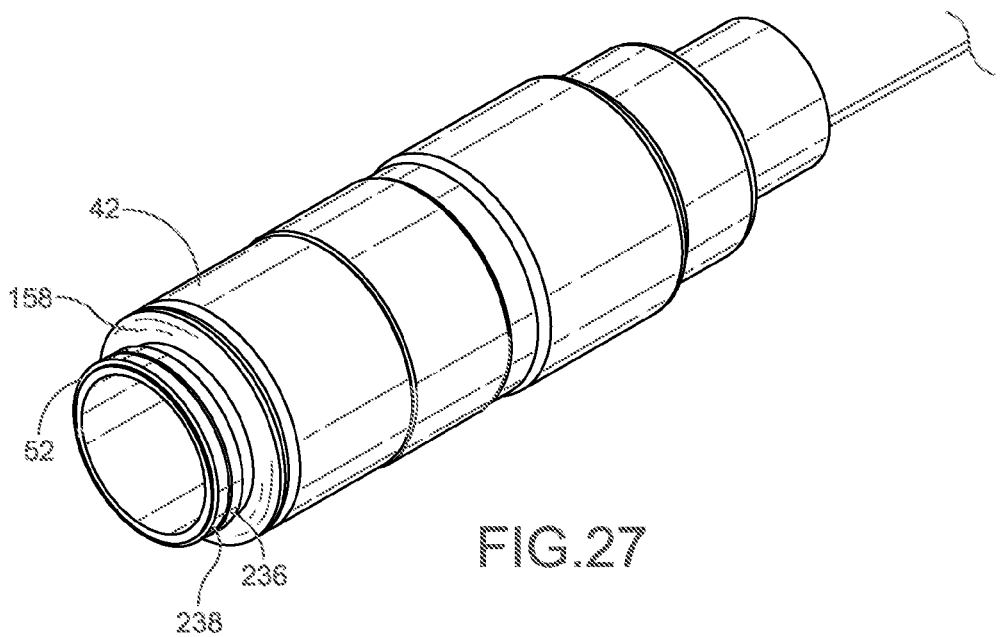
FIG. 27 is a somewhat perspective view of the outer and inner barrels of FIG. 27 but with the ligating bands mounted on the ligating end of the ligator inner barrel.
Figure 28:
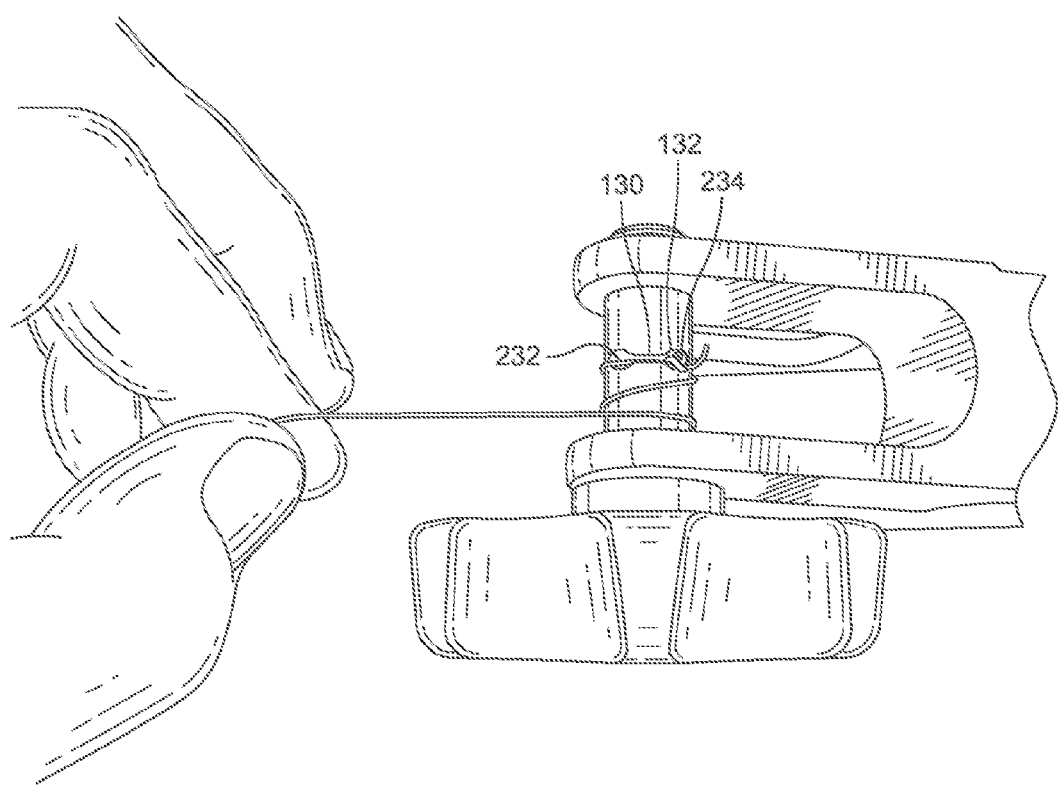
FIG. 28 is top somewhat perspective view of a portion of the band pulling assembly with the pulling cord mounted on, and partially wound around, the rotatable pulling knob in the band pulling assembly.

A method of use of the ligation systems can include the following steps (altered as necessary for any varying structures): 1. With reference to FIG. 1, mount the pulling assembly 46 to the endoscope 41 as explained above. 2. With reference to FIGS. 12, 13, and 24, if necessary, rotate the sealing ring 150 to expose the outer barrel cord channel 161. 3. Thread the inner barrel threads 160 on the mating outer barrel threads 162 all the way into the outer barrel 146 to align the first outer cord passage 168 with the inner barrel cord passage 187, insert a pulling cord 47 through the these cord passages 168, 187, and knot the end 230 of the pulling cord within the inner barrel 148. 4. Insert the un-knotted portion 232 of the pulling cord (extending from the cord passage 187 of the inner barrel 148) through the second cord passage 172 in the outer barrel 146. 5. Pull the un-knotted portion 232 of the pulling cord out of the interior of the outer barrel 146 through its mounting end 154 so that the pulling cord lies within the outer barrel cord channel 161 and the knot 230 is snug inside the inner barrel 48. 6. Rotate the sealing ring 150 to cover the outer barrel cord channel 161 and portion of the pulling cord within the channel 161. 7. With reference now to FIGS. 12, 13, and 25, rotate the inner barrel 148 within the mating threads 162 in the outer barrel 146 to push the inner barrel band mounting end 156 laterally out of the interior of the outer barrel 146, which in turn causes the pulling cord, e.g., 233, to be pulled into the confined area 177 and coil around the inner end 174 of the inner barrel 148 without having the pulling cord wrap 233 onto itself. 8. With reference now to FIG. 25, tie a knot at the free end (not shown) of the pulling cord 234 (which is approximately 4 feet in length). 9. With reference to FIGS. 26 and 27 and when applicable (e.g., when the ligator is not pre-loaded with one or more ligator bands), mount the band-driving washer 158 and one or more of the desired number of ligating bands, e.g., 236, 238, on the ligating end of the ligator 42. 10. With general reference to FIG. 3, pass the free end 232 of the pulling cord 47 (with the help of commercially available biopsy forceps or hooked plastic tubing) through the endoscope's working channel to exit the endoscope access channel 48. 11. With general reference to FIG. 1 and FIG. 13, place the penetrating end of the endoscope 44 into the mounting end of the outer barrel 146. If a proper seal is not achieved, disconnect the penetrating end of the endoscope 44 from the mounting end of the outer barrel 146 and mount the mounting adapter 56 to the penetrating end 44 of the endoscope 41. 12. With reference to FIG. 28, thread the un-knotted end 232 of the pulling cord through the pulling cord slot 130; tie another knot 234 in the un-knotted end 232, and pull the pulling cord through the pulling cord slot 130 so that this latter knot 234 is held in place within the widened cord slot end 132. 13. With general reference back to FIG. 1 and FIG. 28, rotate the knob handle 108 to wind free pulling cord onto the pulling rod 58. 14. With general reference to FIG. 1, insert the mounted ligator 42 into the patient's esophagus. 15. Look through the endoscope viewing lens in the viewing lens end 62 of the endoscope, and locate an esophageal varix. 16. While continuing to look through the endoscope and ligator: press the ligator ligating end 52 to surround the located varix; apply suction via the suction channel of the endoscope to pull the tissue inside the inner barrel 148; rotate the knob handle 108 to wind pulling cord onto the pulling rod 58—continue doing so one index click at a time until the bulge of the varix within the ligating end 52 of the ligator 42 reflects that a ligating band has been ejected from the ligating end 52 to surround the base of the varix as desired. 17. When applicable, repeat steps 15-16 until all desired varices are ligated or all ligating bands have been ejected from the ligator. 18. Withdraw the ligating assembly from the patient's esophagus. Optional additional steps to include when and as applicable: 19. Dispose of the pulling cord except for reusable portions. 20. Dispose of the non-reusable portions of the ligator 42. 21. Treat the reusable portions of the ligator and pulling cord with suitable disinfecting treatment and re-use or store them for later use as applicable.

Referring now to FIG. 1, the resulting ligator assembly is extremely strong, economical, durable, and relatively lightweight. The method of use is accurate, easy, and quick, allowing the practitioner or other operator to see through the endoscope and ligator as desired and without blocking the practitioner's view during the procedure. The assembly preparation steps 1-14 and 18-21 can be performed by personnel other than a medical practitioner to reduce cost and use of time of the medical practitioner.

The ligator may also be made and supplied to users with or without one or more ligating bands preloaded on the ligator. In the latter event, users can load conventional, off-the-shelf rubber bands on the ligator with a conventional band loader.

The ligator and cord pulling assembly may be made of disposable materials. Alternatively, the ligator and cord pulling assembly, or one or more of their components, may be made of materials that can be disinfected and re-used.

This description is not to be construed as limiting. Further, various components of embodiments disclosed herein may be mixed and matched with each other to yield further arrangements of the features disclosed herein.

What is claimed is:

1. A ligating system, comprising:
   a ligating apparatus configured to attach to a distal end of a scope and to hold a ligating band thereon;
   an activating cord configured to extend down a working channel of the scope and attach to the ligating apparatus; and
   a line pulling assembly including:
   a central body;
   a first attachment mechanism on the central body, the first attachment mechanism configured to mount about a proximal end of the scope distal to a working channel access port of the scope;
   a second attachment mechanism coupled with the central body and configured to abut an external periphery of the proximal end of the scope proximal to the working channel access port of the scope, wherein the first and second attachment mechanisms are configured to secure the line pulling assembly onto the proximal end of the scope adjacent to the working channel access port of the scope without covering the access port;
   an access channel through the central body and configured to be in communication with the working channel of the scope, the access channel providing an open inlet to the working channel of the scope when the line pulling assembly is attached to the proximal end of the scope; and
   a winding mechanism attached to the central body, wherein the winding mechanism is configured to pull the activating cord proximally such that the ligating band is removed from the ligating apparatus.

2. The ligating system of claim 1 wherein the access channel is configured to allow a working element to be placed through the working channel of the scope during use of the ligating apparatus.

3. The ligating system of claim 1 wherein the winding mechanism includes a pulling rod configured to attach to a distal end of the activating cord and a knob configured to rotate the pulling rod.

4. The ligating system of claim 3 wherein a central axis of the pulling rod is transverse to a central axis of the access channel.

5. The ligating system of claim 3 wherein the knob includes finger grips or depressions.

6. The ligating system of claim 3 wherein the knob is indexed such that the activating cord is pulled in predetermined increments when the knob is rotated.

7. The ligating system of claim 6 wherein the knob includes index markings configured to mate with index markings on the central body such that the rotating rod stops at fixed increments during rotation thereof.

8. The ligating system of claim 1 wherein the first attachment mechanism is conical.

9. The ligating system of claim 1, wherein the second attachment mechanism comprises a mounting pin connected to the central body.

10. The ligating element of claim 9, wherein the winding mechanism includes a pulling rod around which the activating cord winds, and wherein the mounting pin and the pulling rod are substantially parallel.

11. The ligating system of claim 1 wherein the central body includes opposed arcuate mounting arms configured to sit on either side of a distal end of a handle of the scope.

12. The ligating system of claim 1 wherein the ligating apparatus includes a barrel about which the ligating band is mounted.

13. The ligating system of claim 12 wherein the activating cord extends at least partially around the barrel.

14. The ligating system of claim 1 wherein the ligating apparatus includes an outer barrel mounted about at least a portion of an inner barrel, the inner barrel being rotatable with respect to the outer barrel.

15. The ligating system of claim 14 wherein pulling the activating cord proximally causes the inner barrel to rotate relative to the outer barrel.

16. The ligating system of claim 14 wherein the ligating band is mounted about the inner barrel.

17. The ligating system of claim 1 wherein the ligating apparatus includes an axial passage configured to allow a user to view through the ligating apparatus when the ligating apparatus is attached to the scope.

18. The ligating system of claim 1 wherein the activating cord comprises wire, a plastic line, a monofilament, or a braided line.

19. The ligating system of claim 1 wherein the line pulling assembly comprises plastic, metal, or rubber.

20. The ligating system of claim 1, wherein the first attachment mechanism is configured to mount about a central axis of the scope, the central axis extending through a working end of the scope.

21. The ligating system of claim 1, wherein the first attachment mechanism is a partially open annular element.

* * * * *